United States Patent [19]

Cottens

[11] Patent Number: 5,166,181

[45] Date of Patent: Nov. 24, 1992

[54] HALOGENOALKYLPHENYL-ALCOHOLS, KETONES AND HYDRATES THEREOF

[75] Inventor: Sylvain Cottens, Witterswil, Switzerland

[73] Assignee: Sandoz Ltd., Basel, Switzerland

[21] Appl. No.: 567,875

[22] Filed: Aug. 15, 1990

[30] Foreign Application Priority Data

Aug. 16, 1989 [DE] Fed. Rep. of Germany ....... 3927049

[51] Int. Cl.⁵ .......................................... A61K 31/135
[52] U.S. Cl. .................... 514/653; 514/655; 514/657; 564/342; 564/355; 564/360; 564/428; 564/442
[58] Field of Search ............. 564/384, 366, 360, 355, 564/428, 342; 514/655, 649, 653, 657; 568/862, 772, 814, 799

[56] References Cited

U.S. PATENT DOCUMENTS 2,840,617  6/1958  Shokal ................. 260/635
3,996,279 12/1976  Schlager ............. 260/559 R
4,783,559 11/1988  Matsushita et al. .......... 568/862

OTHER PUBLICATIONS

Fisher et al., "Alzheimer's and Parkinson's Disease" Advances in Behavioral Biology, vol. 29 (1985) pp. 539–549.

Primary Examiner—Richard L. Raymond
Assistant Examiner—Brian M. Burn
Attorney, Agent, or Firm—Gerald D. Sharkin; Robert S. Honor; Thomas O. McGovern

[57] ABSTRACT

Halogenoalkylphenyl-alcohols, ketones and their hydrates of formula I,

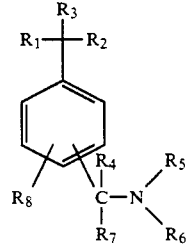

wherein $R_1$ to $R_8$ are as defined in the description, are useful as acetylcholinesterase inhibitors.

13 Claims, No Drawings

HALOGENOALKYLPHENYL-ALCOHOLS, KETONES AND HYDRATES THEREOF

The present invention relates to new halogenoalkyl-phenylalkohols, -ketones and hydrates thereof.

These compounds, hereinafter referred to as new compounds, are compounds of formula I,

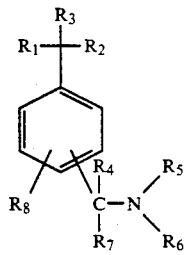

wherein
- $R_1$ is hydrogen or hydroxy,
- $R_2$ is hydroxy or together with $R_1$ forms an oxo group,
- $R_3$ is $(C_{1-4})$alkyl substituted by 1 to 5 halogen atoms,
- $R_4$ is hydrogen or $(C_{1-4})$alkyl,
- $R_5$ and $R_6$ independently are $(C_{1-4})$alkyl,
- $R_7$ is $(C_{1-4})$alkyl and
- $R_8$ is hydrogen or $(C_{1-4})$alkyl, or is in ortho position to the dialkylaminoalkyl rest and together with $R_7$ is $-(CH_2)_n-$ wherein n is 2, 3 or 4, in free base or acid addition salt form.

Depending on the substituents the new compounds may present asymmetrical carbon atoms. The invention includes all resulting stereomers as well as their mixtures, e.g. the racemic mixtures of the enantiomers.

Insofar as above-defined alkyl groups are present in the compounds of formula I, these preferably have 1 or 2 carbon atoms and especially signify methyl.

Halogen in $R_3$ is fluorine, chlorine, bromine or iodine, especially fluorine or chlorine. $R_3$ for example is difluoromethyl, trifluoromethyl, chlorodifluoromethyl or pentafluoroethyl.

$R_4$ is preferably hydrogen.

$R_8$ is preferably hydrogen. The two other substituents on the phenyl are preferably in meta position to each other.

When $R_7$ and $R_8$ together are $-(CH_2)_n-$, then n preferably is 3.

In a group of compounds of formula I,
- $R_1$ and $R_2$ are hydroxy or together form an oxo group,
- $R_3$ is difluoromethyl, trifluoromethyl, chlorodifluoromethyl or pentafluoroethyl,
- $R_4$, $R_5$ and $R_6$ are as defined above,
- $R_7$ is methyl, and
- $R_8$ is hydrogen.

The invention particularly includes the compounds of formula I wherein $R_1$ and $R_2$ each are hydroxy, those wherein $R_3$ is trifluoromethyl, those wherein $R_4$ is hydrogen and $R_5$, $R_6$ and $R_7$ each are methyl, and those wherein $R_8$ is hydrogen and the two other substituents on the phenyl are in meta position to each other, in free base or acid addition salt form.

The preferred compound is the S-1-{3-[1-(dimethylamino)ethyl]phenyl}-2,2,2,-trifluoro-1,1-ethanediol in free base or acid addition salt form.

The present invention also provides a process for the production of a compound of formula I or an acid addition salt thereof, which includes the step of
a) for the production of a compound of formula Ia,

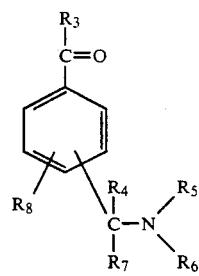

wherein $R_3$ to $R_8$ are as defined above, substituting the halogen in compounds of formula II,

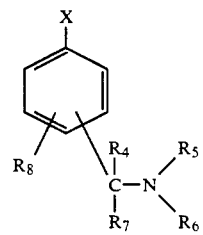

wherein $R_4$ to $R_8$ are as defined above and X is chlorine, bromine or iodine, by a radical $-COR_3$, or
b) for the production of a compound of formula Ib,

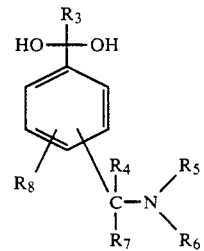

wherein $R_3$ to $R_8$ are as defined above, hydrating a compound of formula Ia, or
c) for the production of a compound of formula Ic,

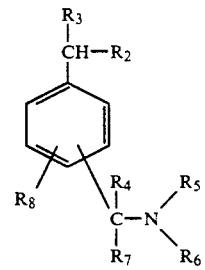

wherein $R_2$ to $R_8$ are as defined above, reducing a compound of formula Ia,
and recovering the thus obtained compound of formula I in free base or acid addition salt form.

In formula II, X is preferably bromine.

Substitution of halogen by a radical $-COR_3$ according to process a) may take place by known methods, for example by halogen-metal exchange with an organolithium such as n-butyllithium or with lithium, followed by a reaction with a reactive derivative of the acid $R_3$—COOH, preferably an ester or an amide. The halogen exchange using lithium is preferably carried out at a low temperature, e.g. between $-100°$ and $-30°$ C., in an aprotic solvent, preferably tetrahydrofuran. The reaction with the acid derivative is conveniently effected at the same low temperature. It is preferable to allow the reaction to take effect for a few hours, and then to add water to the reaction mixture.

Hydration of the compounds of formula Ia according to process b) may take place in known manner, preferably in the presence of an acid, e.g. a mineral acid such as hydrochloric acid or hydrobromic acid.

Reduction of the compounds of formula Ia according to process c) may take place by known methods, using preferably metal hydrides as reduction agents, e.g. lithium aluminium hydride or sodium borohydride.

Working up of the reaction mixtures obtained according to the above processes, and purification of the compounds of formula I thus obtained, may be carried out by known methods.

If desired, enantiomer separation may be effected using known methods, e.g. formation of acid addition salts with optically active acids, e.g. (+)-[resp. (−)]-di-O,O'-p-toluoyl-D-(−)-[resp. L-(+)]-tartaric acid, and fractionated crystallization of the diastereoisomeric acid addition salts.

Acid addition salts may be produced from the free base forms in known manner, and vice-versa.

The starting compounds of formula II may be produced from compounds of formula III

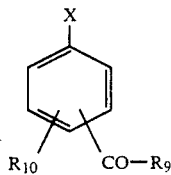

(III)

wherein X is as defined above, $R_9$ is methyl and $R_{10}$ is hydrogen or is in ortho position to the $R_9$—CO-radical and together with $R_9$ is —$(CH_2)_n$— as defined above, using known methods, for example as described in examples 1 and 8.

Insofar as the production of the starting products is not described, these are known or may be produced by known processes, resp. analogously to known processes.

The compounds of formula I and their pharmaceutically acceptable acid addition salts, referred to hereinafter as compounds according to the invention, exhibit pharmacological activity and are therefore useful as pharmaceuticals.

In particular, the compounds according to the invention carry out selective inhibition of the acetylcholinesterase activity in various cerebral regions, which was established in the rat ex vivo following administration of doses between 0.3 and 10.0 μmol/kg p.o.

The acetylcholinesterase activity is measured in accordance with the spectrophotometric method described by Elman (Arch. Biochem. Biophys. 82, 70, 1959). Rat's cerebral tissue is homogenised in cold phosphate buffer pH 7.3 (0.25 mM), containing 0.1% Triton X-100. Following centrifugation, aliquots from the clear supernatant are used as a source of enzyme. In this test, using enzyme from various cerebral regions, significant inhibition is established, while enzyme from peripheral organs is little affected.

The compounds according to the invention may therefore be employed as selective acetylcholinesterase inhibitors, e.g. for the treatment of senile dementia, Alzheimer's disease, Huntington's chorea, tardive dyskinesia, hyperkinesia, mania, acute confusional disorders, Down's syndrome, myasthenia gravis, Friedrich's ataxia and pain.

For these indications, the appropriate dosage will, of course, vary depending upon, for example, the compound employed, the host, the mode of administration and the nature and severity of the condition being treated. However, in general, satisfactory results in animals are indicated to be obtained at daily dosages from about 0.01 to about 10 mg/kg animal body weight. In larger mammals, for example humans, an indicated daily dosage is in the range from about 0.1 mg to about 50 mg of a compound according to the invention, especially about 1 to 10 mg, conveniently administered, for example, in divided doses up to four times a day.

The compounds according to the invention may be administered by any conventional route, in particular enterally, preferably orally, for example in the form of tablets or capsules, or parenterally, for example in the form of injectable solutions or suspensions.

The S-1-{3-[1-(dimethylamino)ethyl]phenyl}-2,2,2-trifluoro-1,1-ethanediol in free base or acid addition salt form is the preferred compound. After administering this compound in the above mentioned ex vivo test at doses between 0.3 and 10.0 μmol/kg p.o., strong inhibition is established e.g. with enzyme from the cortex, hippocampus, corpus striatum and pons/medulla, while enzyme from the heart is not affected.

The present invention also provides pharmaceutical compositions comprising a compound according to the invention in association with at least one pharmaceutical carrier or diluent. Such compositions may be manufactured in conventional manner. Unit dosage forms contain, for example, from about 0.025 mg to about 25 mg of a compound according to this invention.

The following examples illustrate the invention. The temperatures are given in degrees Celsius and are uncorrected.

EXAMPLE 1

1-{3-[1-(dimethylamino)ethyl]phenyl}-2,2,2-trifluoroethanone 10 g of 3-bromo-N,N,α-trimethylbenzenemethanamine are dissolved in 80 ml of tetrahydrofuran and cooled to $-77°$. 30 ml (48 mMol) of n-butyllithium in hexane is added in drops, and the reaction mixture is stirred at this temperature for ten minutes. Then, 8.0 g (47 mMol) of ethyl trifluoroacetate are added. After 2 hours, the reaction mixture is mixed with 10 ml of water and poured onto 600 ml of ethyl acetate. The organic phase is washed with water, dried and finally concentrated. After distillation of the remaining oil, the pure trifluoromethyl ketone is obtained; b.p.: 75°–80°/5 mmHg; $^1$H-NMR (CDCl3, TMS) δ: 1.38 (d, J=7, 3H); 2.20 (s, 3H); 3.35 (q, J=7, 1H); 7.51 (t, J=8, 1H); 7.70 (d, J=8, 1H); 7.93 (d, J=8, 1H); 8.00 (s, 1H).

The 3-bromo-N,N,α-trimethylbenzenemethanamine used as the starting material may be produced as follows:

60 g (0.30 mols) of 3-bromoacetophenone are dissolved in 800 ml of ethanol and mixed with 250 ml of dimethylamine. The pH of the solution is adjusted to 6.5 with acetic acid. The reaction mixture is then cooled to 0° and mixed with 19 g of sodium cyanoborohydride. After stirring for 2 days at room temperature, the reaction mixture is concentrated. The residue is mixed with 800 ml of water and acidified. The solution is then extracted twice with 400 ml of ether, the aqueous phase is rendered basic and extraction follows 3× with 400 ml of ether. The combined organic extracts are dried and concentrated. After distillation of the residue, the 3-bromo-N,N,α-trimethylbenzenemethanamine is obtained; b.p.: 98°–100°/10 mmHg.

EXAMPLE 2

1-{3-[1-(dimethylamino)ethyl]phenyl}-2,2,2-trifluoro-1,1-ethanediol 5 g of the compound obtained in example 1 are dissolved in 100 ml of ether, and the solution is acidified with an excess of hydrogen chloride. After recrystallisation of the precipitated solid from acetone/water, the pure hydrochloride of the title compound is obtained. M.p.: 137°–139°.

EXAMPLE 3

S-1-{3-[1-(dimethylamino)ethyl]phenyl}-2,2,2-trifluoroethanone 10.0 g of racemic 3-bromo-N,N,α-trimethylbenzenemethanamine and 10.1 g of (+)-di-O,O'-p-toluyl-D-tartaric acid monohydrate are dissolved in 700 ml of acetone whilst hot. The salt which precipitates after cooling is filtered off and recrystallised from a mixture of 1 liter of acetone and 25 ml of methanol. By partitioning the crystallisate obtained between 10% Na$_2$CO$_3$ and ether, the (−)-enantiomer of 3-bromo-N,N,α-trimethylbenzenemethanamine is obtained; $[\alpha]_D^{20} = -41.1°$ (c=1, MeOH).

The (−)-3-bromo-N,N,α-trimethylbenzenemethanamine is converted into the title compound using the method described in example 1; $[\alpha]_D^{20} = -44.8°$ (c=1, acetone).

EXAMPLE 4

S-1-{3-[1-(dimethylamino)ethyl]phenyl}-2,2,2-trifluoro-1,1-ethanediol

By treating (−)-1-{3-[1-(dimethylamino)ethyl]phenyl}-2,2,2-trifluoroethanone with HCl in ether, as described in example 2, the S-1-{3-[1-(dimethylamino)ethyl]phenyl}-2,2,2-trifluoro-1,1-ethanediol is obtained in the form of the hydrochloride; $[\alpha]_D^{20} = -6.5°$ (c=1, water).

$^1$H-NMR (DMSO-d$_6$): δ=1.65 (d, J=6, 3H); 2.48 (d, J=5, 3H); 2.71 (d, J=5, 3H); 4.5–4.6 (m, 1H); 7.52 (t, J=8, 1H); 7.1–7.2 (m, 5H); 11.1 (br. s, 1H).

MS (FAB): 264 (MH+, 100%); 219 (38%).

The following compounds (examples 5 to 9) are obtained analogously to example 1:

EXAMPLE 5

1-{3-[1-(dimethylamino)ethyl]phenyl}-2,2-difluoroethanone $^1$H-NMR (CDCl$_3$): δ=1.39 (d, J=7, 3H); 2.20 (s, 6H); 3.36 (q, J=7, 1H); 6.33 (t, J=54, 1H); 7.50 (t, J=8, 1H); 7.67 (d, J=8, 1H); 8.0 (m, 2H).

MS: 227 (18%); 212 (100%); 133 (75%); 72 (95%).

EXAMPLE 6

2-chloro-1-{3-[1-(dimethylamino)ethyl]phenyl}-2,2-difluoroethanone $^1$H-NMR (CDCl$_3$): δ=1.38 (d, J=7, 3H); 2.19 (s, 6H); 3.35 (q, J=7, 1H); 7.48 (t, J=8, 1H); 7.68 (d, J=8, 1H); 8.0 (m, 2H).

MS: 263 (2%); 261 (5%); 248 (18%); 246 (52%); 72 (100%).

EXAMPLE 7

1-{3-[1-(dimethylamino)ethyl]phenyl}-2,2,3,3,3-pentafluoropropanone $^1$H-NMR (CDCl$_3$): δ=1.38 (d, J=7, 3H); 2.20 (s, 6H); 3.35 (q, J=7, 1H); 7.50 (t, J=8, 1H); 7.70 (d, 1H); 8.0 (m, J=8, 2H).

EXAMPLE 8

1-(5-dimethylamino-5,6,7,8-tetrahydro-1-naphthalenyl)-2,2,2-trifluoroethanone $^1$H-NMR (CDCl$_3$): δ=1.6–1.7 (m, 2H); 1.9–2.1 (m, 2H); 2.25 (s, 6H); 2.9 (m, 2H); 3.7–3.8 (m, 1H); 7.32 (t, J=7, 1H); 7.71 (d, J=7, 1H); 8.03 (d, J=7, 1H).

MS: 271 (30%); 242 (30%); 226 (50%); 157 (100%).

The starting material may be produced as follows:

8.5 of 5-bromotetralone are dissolved in 100 ml of ethanol, and 25 ml of a 33% solution of methylamine in ethanol are added. The mixture is cooled to 5° and the pH is adjusted to 6–7 with acetic acid. Then 2.5 g of sodium cyanoborohydride are added in portions. The reaction mixture is then stirred at room temperature during 36 hours. The solvent is evaporated and the residue is added to 1N NaOH. The aqueous phase is extracted 3× with ether and the combined organic extracts are dried on Na$_2$SO$_4$ and evaporated. The remaining oil (8.7 g) is dissolved in 100 ml of methanol and 6 ml of a 33% aqueous solution of formaldehyde are added. The mixture is cooled to 5° and 2.8 g of sodium borohydride are added. After stirring at room temperature for 24 hours, the reaction mixture is concentrated and the residue is added to 1N HCl. The aqueous phase is washed 2× with ether. The pH is then adjusted to 10 with 30% NaOH and extraction follows 3× with ether. The organic extracts are dried on Na$_2$SO$_4$ and concentrated. The 5-bromo-N,N-dimethyl-1,2,3,4-tetrahydro-1-naphthalenylamine is obtained.

$^1$H-NMR (CDCl$_3$): δ=1.6 (m, 2H); 1.9 (m, 1H); 2.1 (m, 1H); 2.24 (s, 6H); 2.6 (m, 1H); 2.8 (m, 1H); 3.7 (m, 1H); 7.03 (t, J=7, 1H); 7.40 (d, J=7, 1H); 7.62 (d, J=7, 1H).

EXAMPLE 9

1-(8-dimethylamino-5,6,7,8-tetrahydro-2-naphthalenyl)-2,2,2-trifluoroethanone $^1$H-NMR (CDCl3): δ=1.6–1.7 (m, 2H); 1.9–2.1 (m, 2H); 2.27 (s, 6H); 2.8–2.9 (m, 2H); 3.7–3.8 (m, 1H); 7.21 (d, J=7, 1H); 7.81 (d, J=7, 1H); 8.4 (s, 1H).

MS: 271 (50%); 242 (95%); 226 (75%); 157 (100%).

EXAMPLE 10

1-{3-[1-(dimethylamino)ethyl]phenyl}-2,2,2-trifluoroethanol 30 mg of the ketone obtained in example 3 are dissolved in 6 ml of tetrahydrofuran and added in drops at 0° to a suspension of 100 mg of lithiumaluminium hydride in 4 ml of tetrahydrofuran. After 5 hours cooling at room temperature, 1 ml of methanol and 0.5 ml of water are added in drops. Then, the reaction mixture is filtered on hyflo and the filtrate is concentrated by evaporation. One obtains 452 mg of a diastereomeric mixture of the title compound.

$^1$H-NMR (CDCl3): $\delta = 1.37$ (d, J=6) and 1.38 (d, J=6) together 3H; 2.23 (s, 6H); 3.21 (q, J=6) and 3.36 (q, J=6) together 1H; 4.58 (q, J=6) and 4.85 (q, J=6) together 1H; 5.9 (br. s, 1H); 7.3–7.5 (m, 4H).

MS: 248 (100%); 232 (25%); 203 (40%).

What we claim is:

1. A compound which is of formula I,

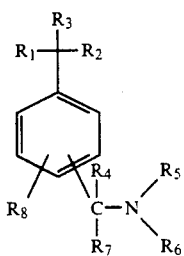

wherein $R_1$ is hydrogen or hydroxy, $R_2$ is hydroxy or together with $R_1$ forms an oxo group, $R_3$ is $(C_{1-4})$alkyl substituted by 1 to 5 halogen atoms, $R_4$ is hydrogen or $(C_{1-4})$alkyl, $R_5$ and $R_6$ independently are $(C_{1-4})$alkyl, $R_7$ is $(C_{1-4})$alkyl and $R_8$ is hydrogen or $(C_{1-4})$alkyl, or is in ortho position to the dialkylaminoalkyl and together with $R_7$ is —(CH$_2$)n— wherein n is 2, 3 or 4, in free base or acid addition salt form.

2. A compound of claim 1 wherein $R_1$ and $R_2$ are hydroxy or together form an oxo group, $R_3$ is difluoromethyl, trifluoromethyl, chlorodifluoromethyl or pentafluoroethyl, $R_4$, $R_5$ and $R_6$ are as defined above, $R_7$ is methyl, and $R_8$ is hydrogen.

3. A compound of claim 1 which is the S-1-{3-[1-(dimethylamino)ethyl]phenyl}-2,2,2-trifluoro-1,1-ethanediol in free base or acid addition salt form.

4. A pharmaceutical composition comprising a therapeutically effective amount of a compound according to claim 1, in association with a pharmaceutical carrier or diluent.

5. The compound according to claim 1 which is 1-{3-[1-(dimethylamino)ethyl]phenyl}-2,2,2-trifluoroethanone in free base or acid addition salt form.

6. The compound according to claim 1 which is 1-{3-[1-(dimethylamino)ethyl]phenyl}-2,2,2-trifluoro-1,1-ethanediol in free base or acid addition salt form.

7. The compound according to claim 1 which is S-1-{3-[1-(dimethylamino)ethyl]phenyl}-2,2,2-trifluoroethanone in free base or acid addition salt form.

8. The compound according to claim 1 which is 1-{3-[1-(dimethylamino)ethyl]phenyl}-2,2-difluoroethanone in free base or acid addition salt form.

9. The compound according to claim 1 which is 2-chloro-1-{3-[1-(dimethylamino)ethyl]phenyl}-2,2-difluoroethanone in free base or acid addition salt form.

10. The compound according to claim 1 which is 1-{3-[1-(dimethylamino)ethyl]phenyl}-2,2,3,3,3-pentafluoropropanone in free base or acid addition salt form.

11. The compound according to claim 1 which is 1-(5-dimethylamino-5,6,7,8-tetrahydro-1-naphthalenyl)-2,2,2-trifluoroethanone in free base or acid addition salt form.

12. The compound according to claim 1 which is 1-(8-dimethylamino-5,6,7,8-tetrahydro-2-naphthalenyl)-2,2,2-trifluoroethanone in free base or acid addition salt form.

13. The compound according to claim 1 which is 1-{3-[1-(dimethylamino)ethyl]phenyl}-2,2,2-trifluoroethanol in free base or acid addition salt form.

* * * * *